US 6,654,703 B2

(12) United States Patent
Wu

(10) Patent No.: US 6,654,703 B2
(45) Date of Patent: Nov. 25, 2003

(54) METHOD FOR ESTIMATING REPAIR ACCURACY OF A MASK SHOP

(75) Inventor: Yuan-Hsun Wu, Jungli (TW)

(73) Assignee: Nanya Technology Corporation, Taoyuan (TW)

( * ) Notice: Subject to any disclaimer, the term of this patent is extended or adjusted under 35 U.S.C. 154(b) by 65 days.

(21) Appl. No.: 10/045,840

(22) Filed: Nov. 8, 2001

(65) Prior Publication Data

US 2003/0065475 A1 Apr. 3, 2003

(30) Foreign Application Priority Data

Sep. 28, 2001 (TW) ........................................ 90124105 A

(51) Int. Cl.[7] ................................................ G03F 9/00
(52) U.S. Cl. ............................. 702/155; 430/5; 716/21; 382/144; 382/145; 250/310
(58) Field of Search ......................... 702/95, 155, 157, 702/159; 356/237.3, 239.9; 430/5, 30; 716/21; 382/144, 145; 257/798; 250/310, 492

(56) References Cited

U.S. PATENT DOCUMENTS

| | | | | | |
|---|---|---|---|---|---|
| 5,391,441 | A | * | 2/1995 | Imai et al. | 430/5 |
| 6,322,935 | B1 | * | 11/2001 | Smith | 430/5 |
| 6,335,129 | B1 | * | 1/2002 | Asano et al. | 430/5 |
| 6,415,431 | B1 | * | 7/2002 | Neary | 716/21 |

* cited by examiner

*Primary Examiner*—John Barlow
*Assistant Examiner*—John Le
(74) *Attorney, Agent, or Firm*—Ladas & Parry

(57) ABSTRACT

A method for estimating repair accuracy of a mask shop. The method includes the steps of providing a mask having a light-shielding layer with a pattern of a plurality of lines, each of which has a defect, using the mask shop to repair the defects, measuring first widths of the lines where the defects are repaired and second and third widths of the lines aside where the defects are repaired, and calculating ratios of mean values of the second and third widths to the first widths for estimating the repair accuracy.

10 Claims, 4 Drawing Sheets

METHOD FOR ESTIMATING REPAIR ACCURACY OF A MASK SHOP

BACKGROUND OF THE INVENTION

1. Field of the Invention

The present invention relates to a method for estimating repair accuracy of a mask shop, which provides a basis for engineers to determine a qualified mask shop.

2. Description of the Prior Art

Masks are frequently used in a semiconductor manufacturing process. A typical mask comprises a transparent substrate such as a quartz substrate and a light-shielding or absorbing layer such as a chrome layer with a thickness of 1000 Å on the substrate. A phase-shift mask further comprises a layer generating a phase shift for the light penetrating therethrough.

A typical mask manufacturing process comprises the steps of depositing a chrome layer on a quartz substrate, depositing a photoresist layer on the chrome layer, patterning the chrome layer by etching under the masking of the photoresist layer processed by e-beam writing and developing.

Defects on the chrome layer are usually generated after the previously described steps. They include clear defects which are missing parts of the chrome layer and opaque defects which are redundant parts of the chrome layer. A further step of chrome depositing is needed to repair the clear defects. As for repairing the opaque defects, a step of chrome sputtering using FIB (Focus Ion Beam) is implemented.

The repair accuracy of the mask shop is very important due to the shrinkage of ICs and since defects of the chrome layer always exist. Engineers are eagerly to have a estimation basis of the repair accuracy to determine a qualified mask shop.

SUMMARY OF THE INVENTION

Therefore, the object of the present invention is to provide an estimating method for the repair accuracy for the engineers to determine a qualified mask shop.

The present invention provides a method for estimating a repair accuracy of a mask shop. The method has the steps of providing a mask having a light-shielding layer with a pattern of a plurality of lines, each of which has a defect, using the mask shop to repair the defects, measuring first widths of the lines where the defects are repaired and second and third widths of the lines aside where the defects are repaired, and calculating ratios of means of the second and third widths to the first widths for estimating the repair accuracy.

Therefore, by using the mask shop to repair the defects on the vertical and horizontal line with different widths, and statistically calculating the errors of the results, the repair accuracy of the mask shop is determined.

BRIEF DESCRIPTION OF THE DRAWINGS

The following detailed description, given by way of example and not intended to limit the invention solely to the embodiments described herein, will best be understood in conjunction with the accompanying drawings, in which.

DETAILED DESCRIPTION OF THE INVENTION

Figure 1A:
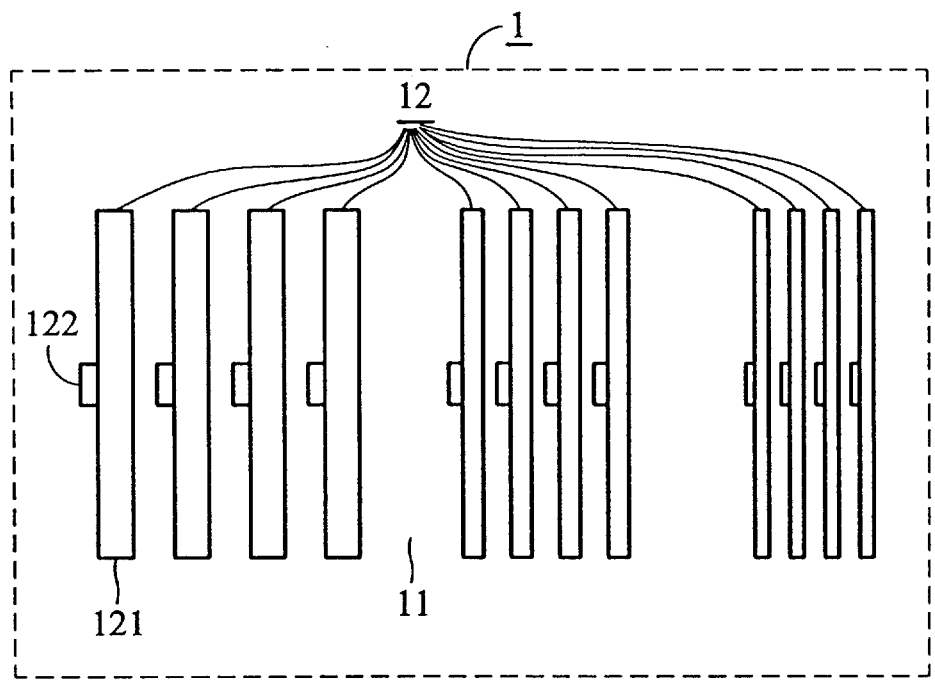
FIGS. 1A and 1B are diagrams showing a pattern of vertical lines on a chrome layer according to one embodiment of the invention.

FIG. 1A is a diagram showing a pattern of vertical lines on a chrome layer of a mask according to a first embodiment of the invention.

The mask comprises a transparent quartz substrate 11 and a chrome layer 12. The chrome layer 12 has a pattern of lines comprising vertical lines 121 with defects 122 protruding from the lines 121. The widths of the vertical lines 121 are represented by "a" and the widths of the protruding defects 122 along the direction vertical to the lines 121 are 0.5a. The widths a range from 0.5 $\mu$m to 2 $\mu$m. In this embodiment, the widths a are 0.6, 0.9 and 1.2 $\mu$m.

Figure 1B:
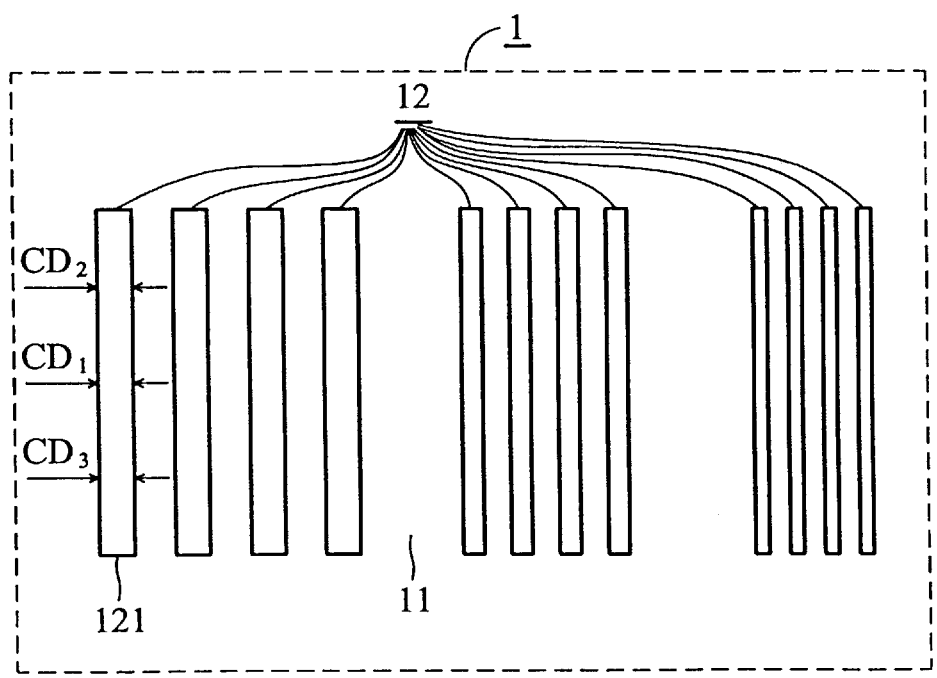

As shown in FIG. 1B, the defects 122 are removed by a mask shop to be estimated using FIB sputtering. The widths $CD_1$ of the lines 121 where the defects 122 are repaired, and the widths $CD_2$ and $CD_3$ of the lines 121 aside where the defects 122 are repaired are measured. Ratios $CD_{bias}$ for each lines 121 are calculated according to the following equation.

$$CD_{bias} = \frac{CD_1 - (CD_2 + CD_3)/2}{(CD_2 + CD_3/2}$$

Therefore, the four ratios $CD_{bias}$ are obtained for each group of the lines 121 with width of 0.6, 0.9 and 1.2 $\mu$m. A mean and 3δ value of the ratios $CD_{bias}$ are also obtained for each group. Accordingly, the repair accuracy of the mask shop is estimated. The number of the lines 121 is only for example and is usually more than 4 for a statistically effective estimation.

Figure 2A:
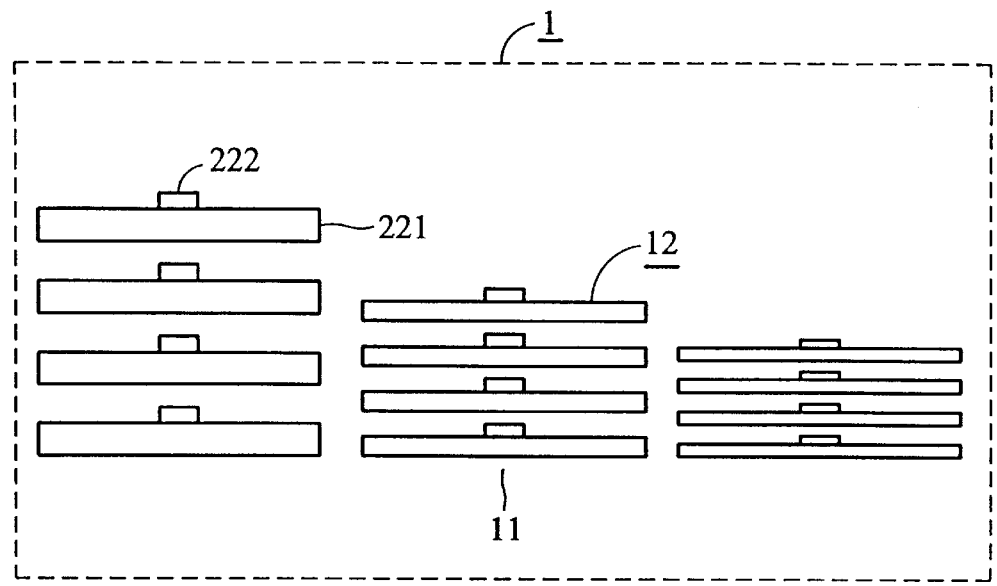
FIGS. 2A and 2B are diagrams showing a pattern of horizontal lines on a chrome layer according to one embodiment of the invention.

FIG. 2A is a diagram showing a pattern of horizontal lines on a chrome layer of a mask according to a second embodiment of the invention. The same elements in FIG. 1A, 1B, 2A and 2B refer to the same symbol.

The mask comprises a transparent quartz substrate 11 and a chrome layer 12. The chrome layer 12 has a pattern of lines comprising horizontal lines 221 with defects 222 protruding from the lines 221. The widths of the horizontal lines 221 are represented by "a" and the widths of the protruding defects 222 along the direction vertical to the lines 221 are 0.5a. The widths a range from 0.5 $\mu$m to 2 $\mu$m. In this embodiment, the widths a are 0.6, 0.9 and 1.2 $\mu$m.

Figure 2B:
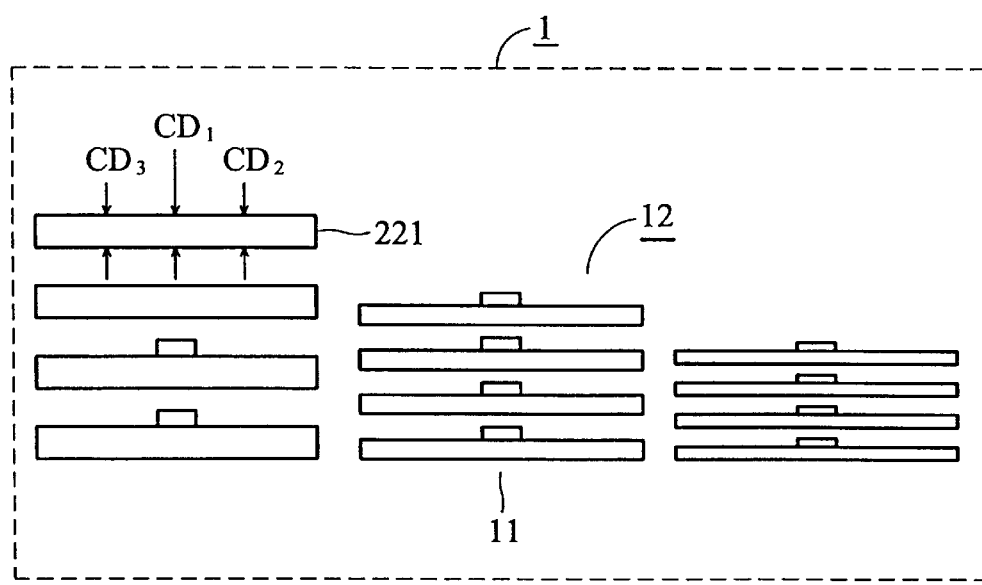

As shown in FIG. 2B, the defects 222 are removed by a mask shop to be estimated using FIB sputtering. The widths $CD_1$ of the lines 221 where the defects 222 are repaired, and the widths $CD_2$ and $CD_3$ of the lines 221 aside where the defects 222 are repaired are measured. Ratios $CD_{bias}$ for each lines 221 are calculated according to the following equation.

$$CD_{bias} = \frac{CD_1 - (CD_2 + CD_3)/2}{(CD_2 + CD_3/2}$$

Therefore, the four ratios $CD_{bias}$ are obtained for each group of the lines 221 with width of 0.6, 0.9 and 1.2 $\mu$m. A mean and 3δ value of the ratios $CD_{bias}$ are also obtained for each group. Accordingly, the repair accuracy of the mask shop is estimated. The number of the lines 221 is only for example and is usually more than 4 for a statistically effective estimation.

Figure 3A:
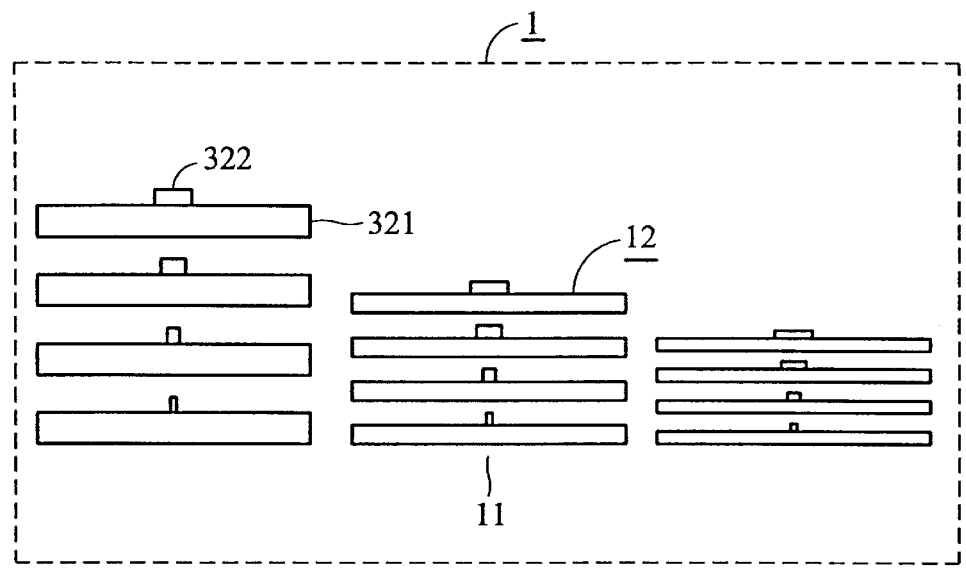
FIGS. 3A and 3B are diagrams showing a pattern of lines having defects with different areas on a chrome layer according to one embodiment of the invention.

FIG. 3A is a diagram showing a pattern of lines with different areas on a chrome layer of a mask according to a third embodiment of the invention. The same elements in FIGS. 1A, 1B, 3A and 3B refer to the same symbol.

The mask comprises a transparent quartz substrate 11 and a chrome layer 12. The chrome layer 12 has a pattern of lines comprising horizontal lines 321 with defects 322 protruding from the lines 321. The widths of the horizontal lines 321 are represented by "a" and the widths of the protruding defects 322 along the direction vertical to the lines 321 are 0.5a. The widths a range from 0.5 $\mu$m to 2 $\mu$m. In this embodiment, the widths a are 0.6, 0.9 and 1.2 $\mu$m. Additionally, the widths of the protruding defects 322 along the direction parallel to the lines 321 are represented by b. The widths b range from 0.3 $\mu$m to 1.5 $\mu$m. In this embodiment, the widths b are 0.3, 0.5, 0.7 and 1.0 $\mu$m.

Figure 3B:
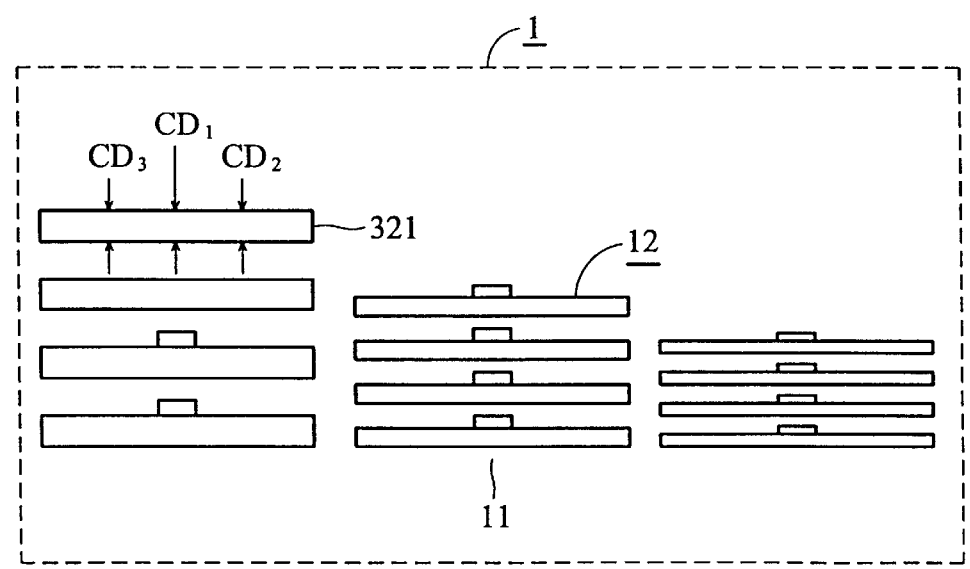

As shown in FIG. 3B, the defects 322 are removed by a mask shop to be estimated using FIB sputtering. The widths $CD_1$ of the lines 321 where the defects 322 are repaired, and the widths $CD_2$ and $CD_3$ of the lines 321 aside where the defects 322 are repaired are measured. Ratios $CD_{bias}$ for each lines 321 are calculated according to the following equation.

$$CD_{bias} = \frac{CD_1 - (CD_2 + CD_3)/2}{(CD_2 + CD_3/2}$$

Therefore, the twelve ratios $CD_{bias}$ are obtained for each lines 321 respectively with width a of 0.6, 0.9 and 1.2 $\mu$m and width b of 0.3, 0.5, 0.7 and 1.0 $\mu$m. However, the number of the lines 321 with a certain width a and b is usually more than 1 (here for example) for a statistically effective estimation. In this case, a mean and 3 $\delta$ value of the ratios $CD_{bias}$ are also obtained for each group of lines with a certain width a and b. Accordingly, the repair accuracy of the mask shop is estimated.

In the third embodiment, the horizontal lines 321 can be substituted for vertical lines.

Figure 4:
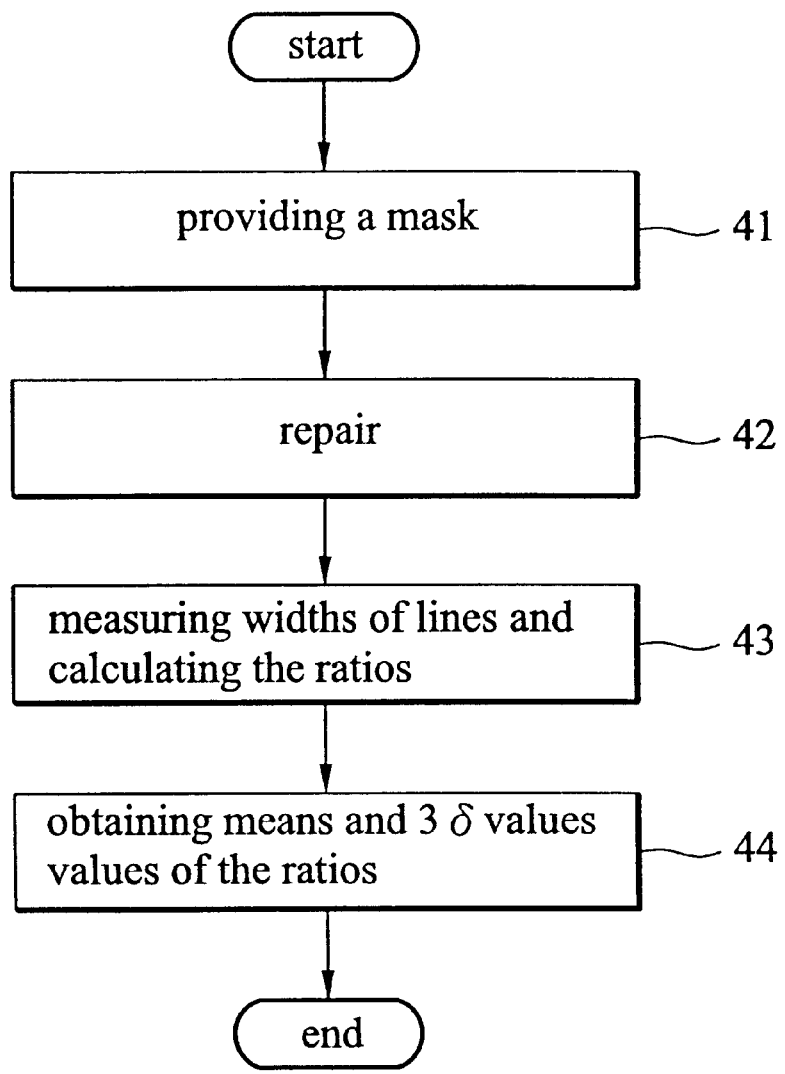
FIG. 4 is a flow chart of a method for estimating a repair accuracy of a mask shop according to one embodiment of the invention.

FIG. 4 is a flow chart of a method for estimating a repair accuracy of a mask shop according to one embodiment of the invention.

In step 41, a mask comprising a chrome layer having a pattern of vertical and horizontal lines with different widths and defects with different areas is provided. The number of the lines with a certain width and defect area is large enough for a statistically effective estimation.

In step 42, the defects are removed by a mask shop to be estimated using FIB chrome sputtering.

In step 43, the widths $CD_1$ of the lines where the defects are repaired, and the widths $CD_2$ and $CD_3$ of the lines aside where the defects 222 are repaired are measured. Ratios $CD_{bias}$ for each lines are calculated according to the following equation.

$$CD_{bias} = \frac{CD_1 - (CD_2 + CD_3)/2}{(CD_2 + CD_3/2}$$

Finally, in step 44, means and 3$\delta$ values of the ratios $CD_{bias}$ for each group of the lines with different widths and defect areas are also obtained. Accordingly, the repair accuracy of the mask shop is estimated.

In conclusion, in the present invention, by using the mask shop to repair the defects on the vertical and horizontal line with different widths and defect areas, and statistically calculating the means and 3 $\delta$ values of the ratios $CD_{bias}$ defined in the invention, the repair accuracy of the mask shop is determined. This provides a basis for engineers to determine a qualified mask shop.

While the invention has been described by way of example and in terms of the preferred embodiment, it is to be understood that the invention is not limited to the disclosed embodiments. On the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A method for estimating repair accuracy of a mask shop comprising the steps of:

providing a mask having a light-shielding layer with a pattern of a plurality of lines, each of which has a defect;

using the mask shop to repair the defects;

measuring first widths of the lines where the defects are repaired and second and third widths of the lines aside where the defects are repaired; and calculating ratios of means of the second and third widths to the first widths for estimating the repair accuracy.

2. The method as claimed in claim 1 further comprising the step of: calculating a mean and 3$\delta$ value of the ratios.

3. The method as claimed in claim 1 wherein the lines comprises a plurality of vertical and horizontal lines.

4. The method as claimed in claim 3 wherein widths of the lines range from 0.5 $\mu$m to 2 $\mu$m.

5. The method as claimed in claim 1 wherein widths of the defects along the lines range from 0.3 $\mu$m to 1.5 $\mu$m.

6. The method as claimed in claim 1 wherein the defects protrude form the lines.

7. The method as claimed in claim 1 wherein the light-shielding layer is a chrome layer.

8. The method as claimed in claim 1 wherein the widths $CD_1$ of the lines where the defects are repaired, and the widths $CD_2$ and $CD_3$ of the lines aside where the defects are repaired are measured and the ratios $CD_{bias}$ for each lines are calculated according to the following equation:

$$CD_{bias} = \frac{CD_1 - (CD_2 + CD_3)/2}{(CD_2 + CD_3/2}.$$

9. The method as claimed in claim 8 wherein the widths $CD_1$ of the lines where the defects are repaired, and the widths $CD_2$ and $CD_3$ of the lines aside where the defects are repaired are 0.6, 0.9 and 1.2 $\mu$m.

10. The method as claimed in 8 wherein the repair accuracy of the mask shop is determined be statistically calculating the means and 3$\delta$ values of the ratios of $$CD_{bias} = \frac{CD_1 - (CD_2 + CD_3)/2}{(CD_2 + CD_3/2}.$$

* * * * *